US010729329B2

(12) United States Patent
Hiltner et al.

(10) Patent No.: US 10,729,329 B2
(45) Date of Patent: Aug. 4, 2020

(54) FIBER OPTIC SENSOR ASSEMBLY FOR SENSOR DELIVERY DEVICE

(71) Applicant: ACIST Medical Systems, Inc., Eden Prairie, MN (US)

(72) Inventors: Jason F. Hiltner, Minnetonka, MN (US); Simon Furnish, Louisville, KY (US); James Lamar Gray, II, New Albany, IN (US); William K. Dierking, Louisville, KY (US); Alan Evans, Otsego, MN (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 1092 days.

(21) Appl. No.: 14/969,062

(22) Filed: Dec. 15, 2015

(65) Prior Publication Data
US 2016/0157727 A1   Jun. 9, 2016

Related U.S. Application Data

(63) Continuation of application No. 13/828,452, filed on Mar. 14, 2013, now Pat. No. 9,241,641.
(Continued)

(51) Int. Cl.
*A61B 5/00* (2006.01)
*A61B 5/0215* (2006.01)

(52) U.S. Cl.
CPC ........ *A61B 5/0084* (2013.01); *A61B 5/02152* (2013.01); *A61B 5/02154* (2013.01);
(Continued)

(58) Field of Classification Search
CPC ..... A61B 5/02154; A61B 1/00; A61B 1/0002; A61B 1/00013; A61B 1/00064;
(Continued)

(56) References Cited

U.S. PATENT DOCUMENTS 3,863,504 A  2/1975 Borsanyi
3,868,844 A  3/1975 Klein et al.
(Continued)

FOREIGN PATENT DOCUMENTS

CN   1913825 A   2/2007
CN  101184977 A   5/2008
(Continued)

OTHER PUBLICATIONS

Conrad, "Pressure-Flow Relationships in Collapsible Tubes," IEEE Transactions on Biomedical Engineering, vol. BME-16, No. 4, 1969, p. 284.
(Continued)

*Primary Examiner* — Jeffrey G Hoekstra
*Assistant Examiner* — Katherine M McDonald
(74) *Attorney, Agent, or Firm* — Fredrikson & Byron, P.A.

(57) ABSTRACT

Methods and sensor delivery devices for monitoring a fluid pressure within a vascular structure, the devices including an elongated sheath sized for sliding along a guidewire, a sensor assembly including a fiber optic sensor, a housing surrounding the sensor, a first cavity between the distal end of the sensor and a distal aperture of the housing, a filler extending from at least the distal end of the housing distally and tapering inward toward the outer surface of the sheath, a second cavity in the filler with an opening at the outer surface of the filler and adjoining the distal aperture of the housing, and an optical fiber. The sensor delivery device may also include an outer layer that partially covers the second cavity with an aperture over the opening of the second cavity.

20 Claims, 4 Drawing Sheets

Related U.S. Application Data (60) Provisional application No. 61/673,840, filed on Jul. 20, 2012.

(52) U.S. Cl.
CPC .......... *A61B 5/6851* (2013.01); *A61B 5/6852* (2013.01); *A61B 2562/0247* (2013.01); *A61B 2562/0266* (2013.01)

(58) Field of Classification Search
CPC ............ A61B 1/00096; A61B 1/00165; A61B 5/6851; A61B 5/02152; A61B 5/0084; A61B 5/6852; A61B 2562/0247; A61B 2562/0266
See application file for complete search history.

(56) References Cited

U.S. PATENT DOCUMENTS

| | | | |
|---|---|---|---|
| 4,226,124 A | 10/1980 | Kersten | |
| 4,227,420 A | 10/1980 | Lamadrid | |
| 4,274,423 A | 6/1981 | Mizuno | |
| 4,314,480 A | 2/1982 | Becker | |
| 4,375,182 A | 3/1983 | Zavoda | |
| 4,722,348 A | 2/1988 | Ligtenberg | |
| 4,959,050 A | 9/1990 | Bobo, Jr. | |
| 5,024,099 A | 6/1991 | Lee | |
| 5,031,460 A | 7/1991 | Kanenobu et al. | |
| 5,105,820 A | 4/1992 | Moriuchi et al. | |
| 5,280,786 A | 1/1994 | Wlodarczyk | |
| 5,335,584 A | 8/1994 | Baird | |
| 5,346,470 A | 9/1994 | Hobbs et al. | |
| 5,449,003 A | 9/1995 | Sugimura et al. | |
| 5,808,203 A | 9/1998 | Nolan, Jr. et al. | |
| 6,077,443 A | 6/2000 | Goldau | |
| 6,371,942 B1 | 4/2002 | Schwartz et al. | |
| 6,568,241 B2 | 5/2003 | Cole | |
| 7,094,216 B2 | 8/2006 | Trombley, III et al. | |
| 7,163,385 B2 | 1/2007 | Gharib et al. | |
| 7,373,826 B2 | 5/2008 | Weber et al. | |
| 7,389,788 B2 | 6/2008 | Wilson et al. | |
| 7,610,936 B2 | 11/2009 | Spohn et al. | |
| 7,617,837 B2 | 11/2009 | Wilson et al. | |
| 7,722,557 B2 | 5/2010 | Sano et al. | |
| 7,905,246 B2 | 3/2011 | Wilson et al. | |
| 9,427,515 B1 | 8/2016 | Nystrom | |
| 2003/0122095 A1 | 7/2003 | Wilson et al. | |
| 2004/0010229 A1 | 1/2004 | Houde et al. | |
| 2005/0120773 A1 | 6/2005 | Ohl et al. | |
| 2006/0180202 A1 | 8/2006 | Wilson et al. | |
| 2007/0179422 A1 | 8/2007 | Schnell et al. | |
| 2008/0058720 A1 | 3/2008 | Spohn et al. | |
| 2008/0154214 A1 | 6/2008 | Spohn et al. | |
| 2009/0149743 A1 | 6/2009 | Barron et al. | |
| 2010/0228136 A1 | 9/2010 | Keel et al. | |
| 2010/0234698 A1 | 9/2010 | Manstrom | |
| 2010/0241008 A1 | 9/2010 | Belleville | |
| 2010/0249587 A1 | 9/2010 | Duchon et al. | |
| 2010/0268098 A1 | 10/2010 | Ito et al. | |
| 2011/0009800 A1 | 1/2011 | Dam et al. | |
| 2013/0255390 A1 | 10/2013 | Riley et al. | |
| 2014/0052009 A1 | 2/2014 | Nystrom et al. | |

FOREIGN PATENT DOCUMENTS

| | | |
|---|---|---|
| CN | 101421602 A | 4/2009 |
| DE | 20019067 U1 | 2/2001 |
| EP | 1213035 A1 | 6/2002 |
| EP | 1655044 A2 | 5/2006 |
| JP | S63-59452 A | 3/1988 |
| JP | H08-117332 A | 5/1996 |
| WO | 9854555 A1 | 12/1998 |
| WO | 2002047751 A2 | 6/2002 |
| WO | 03050491 A2 | 6/2003 |
| WO | 2004061399 A2 | 7/2004 |
| WO | 2007050553 A1 | 5/2007 |
| WO | 2010030882 A1 | 3/2010 |
| WO | 2011002744 A1 | 1/2011 |
| WO | 2011113643 A1 | 9/2011 |
| WO | 2012151542 A2 | 11/2012 |
| WO | 2015061723 A2 | 4/2015 |
| WO | 2017018974 A1 | 2/2017 |

OTHER PUBLICATIONS

Force Sensors Line Guide, Honeywell International, Inc., Golden Valley, Minnesota, Jun. 2009, 3 pages.

Kleinman et al., "Equivalence of Fast Flush and Square Wave Testing of Blood Pressure Monitoring Systems," Journal of Clinical Monitoring, vol. 12, 1996, pp. 149-154.

Miller et al., "Cardiovascular Monitoring," Miller's Anesthesia, Churchill Livingstone/Elsevier, 7th Edition, Chpt. 40, 2010, p. 1278.

National Instruments, "Signal Generator Fundamentals," Retrieved from the Internet <http://zone.ni.zone/devzone/cda/tut/p/id/4089>, 2006.

Smiths Medical International Ltd, LogiCal—The Innovative Pressure Transducer System; Literature No. LIT/PV2588; Hythe, Kent, United Kingdom, 2006, 2 pages.

EP Pat. App. No. 19152737.3, Extended European Search Report dated Jun. 11, 2019, 7 pages.

International Patent Application No. PCT/US2013/051038, International Search Report & Written Opinion dated Dec. 5, 2013, 13 pages.

Merit Sensor BP Series Data Sheet (Sep. 19, 2018), 4 pgs.

FIG. 6

FIBER OPTIC SENSOR ASSEMBLY FOR SENSOR DELIVERY DEVICE

PRIORITY

This application is a continuation of U.S. patent application Ser. No. 13/828,452, filed Mar. 14, 2013, and entitled Fiber Optic Sensor Assembly for Sensor Delivery Device, which claims priority to U.S. Patent Application No. 61/673,840 filed Jul. 20, 2012 and entitled Fiber Optic Sensor Assembly for Sensor Delivery Device, the disclosures of both of which are incorporated by reference.

TECHNICAL FIELD

The present application relates to the field of medical device technology and, more particularly, to pressure sensors for measuring fluid pressure in anatomical (e.g., vascular) structures of patients, such as in blood vessels or across heart valves.

BACKGROUND

When pressure measurements are made within a human or animal, such as within the vascular system, the physical characteristics of the environment make obtaining accurate measurements more complicated than other fluid pressure measurements. For example, such sensors are generally non-toxic and small, in order to cause as little trauma to the individual as possible. In many cases, it may be necessary for the measuring device to enter the body in one location but to make the pressure measurement in a different location which may be a significant distance away from the point of entry of the device. It may therefore be necessary to deliver the sensor to the location using a delivery device such as a catheter. Such a pressure sensing device must therefore be capable of being transported to a different location using a delivery device and must further be able to transmit data back out of the body. Finally, when the pressure measurements are made within the arterial system, the pressure is not steady but rather is pulsatile, rising and falling to an upper systolic and lower diastolic pressure with each heartbeat, adding further complexity to the pressure measurement process.

For some patients, it is useful to obtain a pressure measurement within the coronary arteries. In particular, when a sclerotic lesion is present within the coronary arteries, pressure measurements made upstream and downstream of the lesion can be used to determine whether or not an intervention, such as angioplasty or stent placement, is required. Because such measurements may be used as a basis for therapy decisions, it is important that they be accurate. However, the very small size of the coronary arteries, which may be about 2 mm, and which may be further narrowed by sclerotic lesions or complicated by the presence of stents, as well as the pulsatile nature of the blood flow, and the need to avoid causing any trauma to these critical vessels, present challenges to designing pressure sensing systems.

SUMMARY

Various embodiments of the invention are described and shown herein. In one embodiment, a sensor delivery device may be used for monitoring a fluid pressure within a vascular structure of a patient, such as within the coronary arteries. The sensor delivery device may include an elongated tubular sheath sized for sliding along a guidewire and having an outer surface and a sensor assembly. The sensor assembly may include a fiber optic sensor such as a pressure sensor, a housing surrounding the sensor, the housing having a proximal end with a proximal aperture, a distal end with a distal aperture, an inner surface adjoined to the outer surface of the sheath, and an outer surface opposing the inner surface. The sensor assembly may also include a first cavity between the distal end of the sensor and the distal aperture of the housing, a filler extending from at least the distal end and outer surface of the housing distally with an outer surface that tapers inward toward the outer surface of the sheath as the filler extends distally, and a second cavity in the filler. The second cavity may include an opening at the outer surface of the filler and may adjoin the distal aperture of the housing. The opening and apertures are generally useful for providing fluid communication between the sensor and a patient. The sensor delivery device may further include an optical fiber extending along the outer surface of the sheath, passing through the proximal aperture of the housing and adjoined to the sensor at a distal end of the optical fiber. In some embodiments, the sensor delivery device may also include an outer layer overlying the filler and comprising an aperture. The outer layer may partially cover the second cavity and the aperture may overlie the opening of the second aperture. In some embodiments, the outer layer may encircle the sensor assembly, the sheath, and the optical fiber.

The outer surface of the sheath may form a bottom of the second cavity, the distal end of the housing may form a proximal end of the cavity, the filler material itself may form the distal end of the second cavity and the opposing side surfaces of the second cavity, and the outer layer forms a top of the second cavity.

In some embodiments, the filler surrounds all of the housing except the bottom surface of the housing which abuts the sheath. In some embodiments, the filler may extend proximally from the proximal end and outer surface of the housing and taper inwardly toward the outer surface of the sheath as it extends proximally.

In some embodiments, the second cavity has a length from a proximal to a distal end of the second cavity which is greater than a length of the outer layer aperture from a proximal to a distal end of the outer layer aperture. In some embodiments, the outer layer aperture may have an area of between about 0.05 and about 0.5 mm$^2$. In some embodiments, the second cavity may have a volume of between about 0.04 and about 0.12 mm$^3$.

The sheath of the sensor delivery device may include a distal sleeve and a proximal portion adjoined to the distal sleeve, with the optical fiber extending within the proximal portion and with the proximal portion configured to be separate from the guidewire.

Various embodiments also include methods of measuring the intravascular pressure of a patient at a location of interest using any of the sensor delivery devices described above. The method may include inserting the sensor delivery device into the patient's vasculature, advancing the sensor delivery device to the location of interest; and measuring the intravascular pressure at the location of interest using the pressure sensor.

The details of one or more embodiments are set forth in the accompanying drawing figures and the description below. Other features, objects, and advantages will be apparent from the description and attachments. The embodiments shown and described are provided for the purposes of illustration, not limitation.

DETAILED DESCRIPTION

The following detailed description should be read with reference to the accompanying drawings, in which like numerals denote like elements. The drawings, which are not necessarily to scale, depict selected embodiments—other possible embodiments may become readily apparent to those of ordinary skill in the art with the benefit of these teachings. Thus, the embodiments shown in the accompanying drawings and described below are provided for illustrative purposes, and are not intended to limit the scope as called for in the claims appended hereto. Various exemplary embodiments are described herein with reference to the accompanying drawing figures in which like numbers describe like elements. References to above, below, horizontal, vertical, front, back, left, right and the like shall refer to the orientation of the device when it is properly positioned during use.

Various embodiments may be used to measure blood pressure within the coronary arteries of a patient. Such measurements can be used to measure arterial pressure upstream and downstream of a stenotic lesion or other arterial narrowing (such as narrowing due to the presence of a stent), for example, to assess the severity of the condition and to assist in making therapy decisions. Alternatively, various embodiments may be used to assess heart valves or to measure pressure or pressure gradients peripherally within the peripheral vessels, for example.

Fiber optic pressure sensors useful in various embodiments may be delivered to a location of interest using a guidewire based delivery system, for example. One example of such a system is sometimes referred to as a monorail or rapid exchange system. The fiber optic sensor may be used with the monorail pressure system or any other monorail, rapid exchange catheter or any over-the-wire style catheter and may be transported to a location of interest on a distal sleeve. In some embodiments, the sensor is encased within a housing that is further surrounded by a filler, and these elements together form a sensor assembly. The housing may be stainless steel, polyimide or other appropriate material. The housing may be elongated, having a proximal end and a distal end. An optical fiber may extend proximally from the sensor and exit the housing through a proximal aperture in the proximal end of the housing. The housing may also include a distal aperture. In some embodiments, the distal aperture is in the distal end of the housing and is aligned with the diaphragm of the pressure sensor, with a space forming a first cavity between the distal aperture and the sensor.

Because the sensor delivery system may traverse the coronary arteries, various embodiments include a filler to form a tapered distal surface of the sensor assembly. In some embodiments, the filler portion of the sensor assembly tapers inward as it extends distally from the housing in toward the distal sleeve on which it is carried, being thinnest at its distal end. By tapering in this way, the sensor assembly avoids having a blunt end, perpendicular to the guidewire (and therefore also perpendicular to the direction of motion of the distal sleeve), which could make it difficult to advance through narrowed portions of the coronary arteries. In order to allow pressure to be effectively transferred from the surrounding fluid to the sensor, the filler may include a cavity which forms the second cavity (the first cavity being within the housing), located proximal to the proximal aperture of the housing. The second cavity is open at the outer surface of the filler. In this way, pressure is transmitted through the opening of the second cavity, then through the second cavity, the distal aperture of the housing, the first cavity, and to the sensor.

The sensor assembly may be used on any sensor delivery device, such as a guidewire or catheter based systems, for measuring pressure in the arterial system, for example. An example of a one such system, an over-the-wire system described in U.S. Patent Publication Number 2010/0234698, the disclosure of which is incorporated herein by reference. One such sensor delivery system is shown in FIGS. 1-3 and 5. The sensor delivery device 10 includes a distal sleeve 20 having a guidewire lumen 22 for slidably receiving a medical guidewire 30. A sensor assembly 100 is coupled to the distal sleeve 20 and includes sensor 110 which is capable of sensing and/or measuring a physiological parameter of a patient and generating a signal representative of the physiological parameter, such as pressure. Thus, the distal sleeve 20, and hence, the sensor assembly 100, may be positioned within a patient (e.g., within an anatomical structure of a patient, such as within a vein, artery, or other blood vessel, or across a heart valve, for example) by causing the distal sleeve 20 to slide over the medical guidewire 30 to the desired position.

Figure 1:
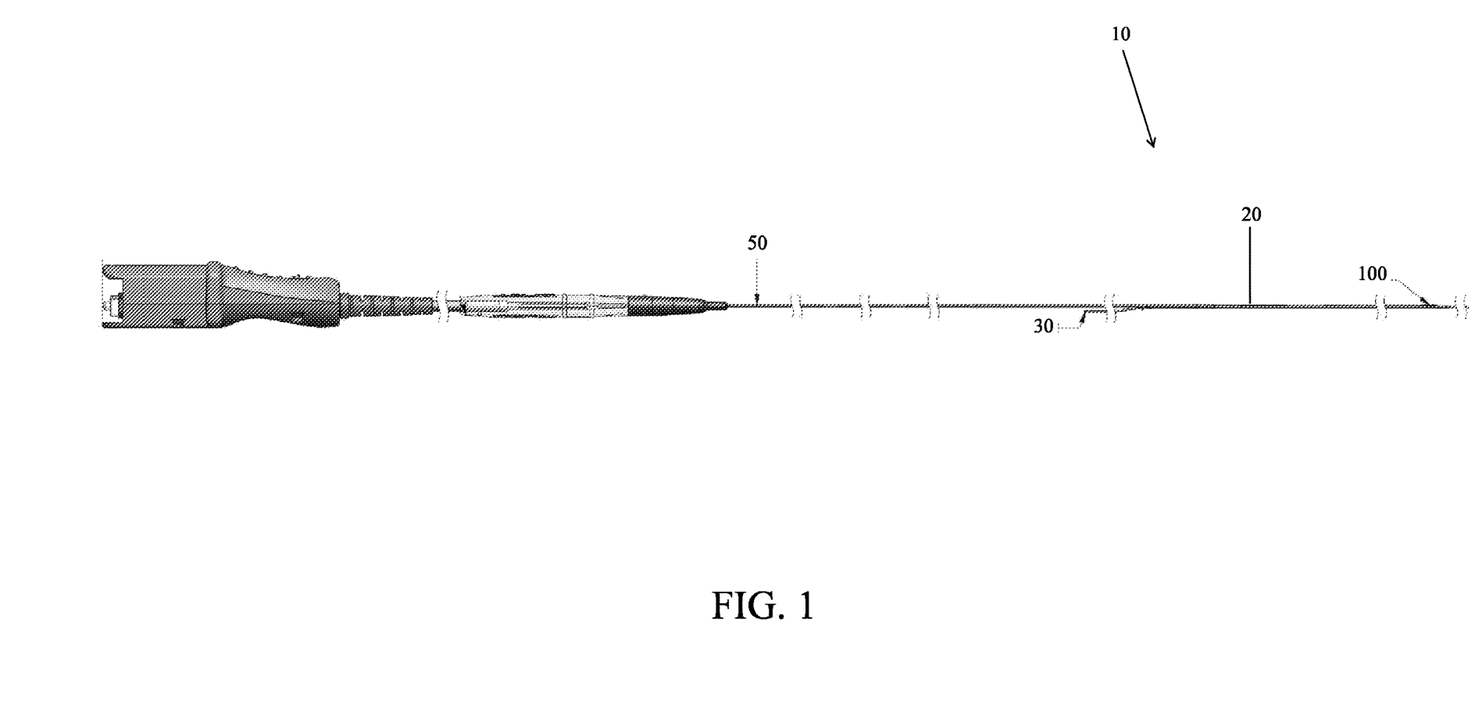
FIG. 1 is a side plan with portions rendered transparent of a sensor delivery device including a sensor assembly according to various embodiments.

The sensor delivery device 10 of FIG. 1 also includes a proximal portion 50, which is coupled to the distal sleeve 20. The proximal portion 50 includes a communication channel for communicating the signal from the sensor 110 to a location outside of the patient (e.g., to a processor, display, computer, monitor, or to another medical device). Communication channel may comprise a fiber optic communication channel in certain preferred embodiments, such as where the sensor 110 is a fiber optic pressure sensor. Alternately, communication channel may comprise an electrically conductive medium, such as one or more electrical conducting wires. Of course, many other forms of communication media may be suitable for transmitting the signal generated by sensor 110 to a location outside of the patient. In some embodiments, the communication channel may comprise any of a variety of fluid and/or non-fluid communication media, such as a wireless communication link, or an infrared capability, or acoustic communications such as ultrasound, as possible examples.

The proximal portion 50 is also adapted to assist an operator (e.g., a physician or other medical staff) in positioning the distal sleeve 20 and the sensor assembly 100 within an anatomical (e.g., vascular) structure of the patient. This may be accomplished by an operator first inserting a "standard" medical guidewire 30 into a patient's vasculature and advancing it past an area of interest. The sensor delivery device 10 is then deployed by "threading" the distal sleeve 20 onto the guidewire 30 such that the lumen 22 slides over the guidewire 30, and advancing the distal sleeve 20 (and the associated sensor assembly 100) by moving (e.g., pushing and/or pulling) the proximal portion 50 until sensor 40 is in the desired location.

In certain embodiments, the size or "footprint" (e.g., the width and/or the cross-sectional area) of device 10 may allow it to fit within certain standard sized guiding catheters. In certain embodiments, the distal sleeve 20 of the device may be substantially concentric with the guidewire 30. The coupling of the proximal portion 50 to the distal sleeve 20 allows the guidewire 30 to separate from the rest of device 10 (e.g., in what is sometimes referred to as a "monorail" catheter configuration).

In the embodiments shown, the sensor assembly 100 is coupled to the outer surface of the distal sleeve 20, at or near the distal end of the distal sleeve 20. Some embodiments may also include a second sensor assembly (not shown), which may be coupled to the outer surface of the distal sleeve 20 at a more proximal location. The sensor 110 within the sensor assembly 100 may be adapted to measure a physiological parameter of a patient, such as a blood parameter (e.g., blood pressure, blood flow rate, temperature, pH, blood oxygen saturation levels, etc.), and generate a signal representative of the physiological parameter. The proximal portion 50 which may be coupled to the distal sleeve 20 includes a communication channel for communicating the physiological signal from the sensor 110 to a location outside of the patient (e.g., to a processor, display, computer, monitor, or to another medical device). The proximal portion 50 may preferably be formed of a material of sufficient stiffness in order to assist an operator (e.g., a physician or other medical staff) in positioning the distal sleeve 20 and the sensor assembly 100 within an anatomical (e.g., vascular) structure of the patient. Depending on the application, the proximal portion 50 (sometimes also referred to as the "delivery tube") may be stiffer and more rigid than the distal sleeve 20 in order to provide a reasonable amount of control to push, pull and otherwise maneuver the device to a physiological location of interest within the patient. Suitable materials for proximal portion 50 include a stainless steel hypotube as well as materials such as nitinol, nylon, and plastic, for example, or composites of multiple materials.

The communication channel may be disposed along an outer surface of proximal portion 50, or may be formed within the proximal portion 50. For example, communication channel may comprise a communication lumen that extends longitudinally through proximal portion 50 in some embodiments. Communication channel may comprise a fiber optic communication channel in certain embodiments, such as where the sensor 110 is a fiber optic pressure sensor. Alternately, communication channel may comprise an electrically conductive medium, such as electrical conducting wires, or other communication media suitable for transmitting the signal generated by sensor 110. In some embodiments, the communication channel comprises a non-fluid communication medium. The communication channel (e.g., a fiber optic cable) may extend distally beyond proximal portion 50 to be coupled to sensor 110 on the distal sleeve. In the embodiment shown, the communication channel 60 extends along the exterior surface of the distal sleeve 20 and into the sensor assembly 100.

Some embodiments the sensor delivery device 10 may include a second sensor assembly which may be coupled to the device 10. For example, a second sensor assembly may be coupled to the proximal portion 50 or distal sleeve 20 such that the first and second sensor are spaced apart sufficiently (e.g., a fixed distance apart) to span a stenotic lesion. This embodiment may offer the ability to measure fractional flow reserve (FFR) without having to reposition device 10, since once sensor could be placed distal of the stenotic lesion to measure pressure distal to the lesion ($P_d$), and the other sensor could be placed proximal of the stenotic lesion to measure pressure distal to the lesion ($P_p$). In some embodiments, the second sensor assembly includes some or all of the various features of the sensor assembly 100 discussed herein.

The sensor assembly 110 described herein may also be used with other pressure sensing systems. For example, while guidewire pressure sensors systems such as the St. Jude Medical Radi System Pressurewire® Certus and Analyzer typically include a strain gauge type sensor, a fiber optic pressure sensor assembly could be used alternatively, along with an optical fiber replacing the electrical conductor typically used in such systems.

Figure 2:
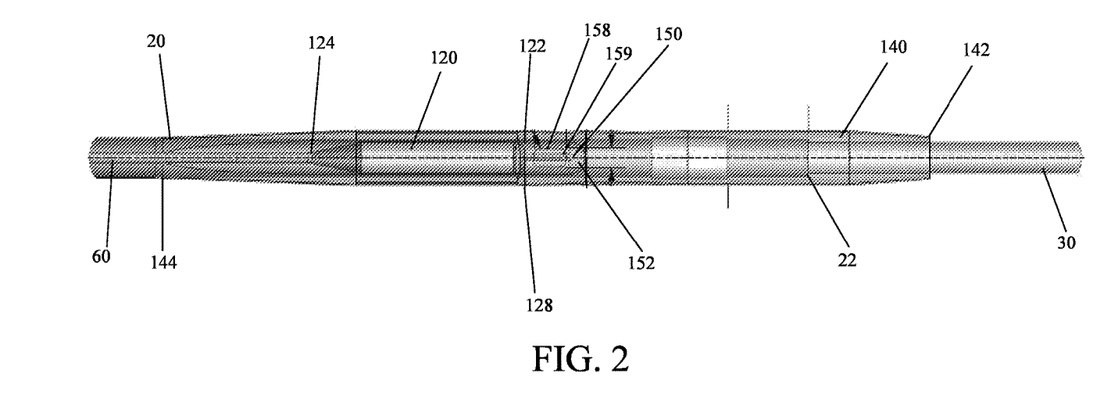
FIG. 2 is a side plan with portions rendered transparent of a portion of the sensor delivery device of FIG. 1 including the sensor assembly.
Figure 3:
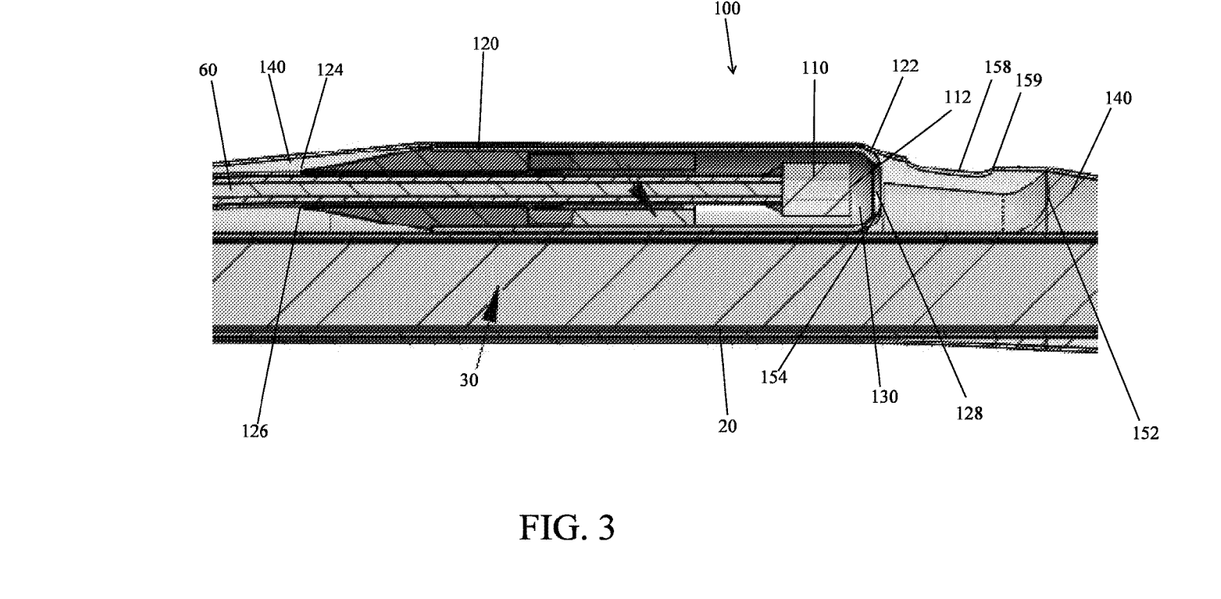
FIG. 3 is a longitudinal cross sectional view of a portion of the sensor assembly of FIG. 2.

A close up perspective view of the sensor assembly 110 on a distal sleeve 20 is shown in FIG. 2, while a longitudinal cross sectional view is shown in FIG. 3. The sensor 110 is located within the housing 120, near the distal end 122 of the housing 120 but separated from the distal end 122 by the first cavity 130. In the embodiment shown, the sensor 110 is a fiber optic pressure sensor adapted to measure blood pressure.

Various embodiments are particularly useful with fiber optic pressure sensors, though they are not limited to such sensors. An example of a fiber optic pressure sensor which may be used in various embodiments is a Fabry-Perot fiber optic pressure sensor, which is a commercially available sensor. Examples of Fabry-Perot fiber optic sensors are the "OPP-M" MEMS-based fiber optic pressure sensor (400 micron size) manufactured by Opsens (Quebec, Canada), and the "FOP-MIV" sensor (515 micron size or 260 micron size) manufactured by Fiso Technologies, Inc. (Quebec, Canada). In certain alternate embodiments, the sensor or sensors 110 may be piezo-resistive pressure sensors (e.g., a MEMS piezo-resistive pressure sensor), and in other embodiments, the sensor or sensors 110 may be capacitive pressure sensors (e.g., a MEMS capacitive pressure sensor). A pressure sensing range from about −50 mm Hg to about +300 mm Hg (relative to atmospheric pressure) may be used for making most physiological measurements with sensor 110, for example.

In embodiments using the Fabry-Perot fiber optic pressure sensor as the sensor 110, such a sensor works by having a reflective diaphragm that varies a cavity length measurement according to the pressure against the diaphragm. Coherent light from a light source travels down the fiber and crosses a small cavity at the sensor end. The reflective diaphragm reflects a portion of the light signal back into the fiber. The reflected light travels back through the fiber to a detector at the light source end of the fiber. The two light waves, the source light and reflected light travel in opposite directions and interfere with each other. The amount of interference will vary depending on the cavity length. The cavity length will change as the diaphragm deflects under pressure. The amount of interference is registered by a fringe pattern detector.

Because such sensors function by transmitting light through the optical fiber and reflecting the light from the diaphragm, the optical fiber is normally perpendicular to the diaphragm. Because the optical fiber extends longitudinally along the sensor delivery device, the result is that the diaphragm of the sensor is perpendicular to the longitudinal axis of the sensor delivery device. Such an orientation of the sensor, with the diaphragm facing distally and perpendicular to the direction of movement of the delivery device through the vasculature, has the potential to interfere with the movement of the delivery device to the desired location for making measurements. Various embodiments therefore reduce or eliminate this interference through the use of the filler, while still providing accurate pressure measurements through the use of cavities and apertures as described herein.

The sensor 110 is encased within a housing 120 which may be a longitudinally extending hollow member which may surround and protect the sensor 110. The housing 120 may be comprised of any rigid or semi-rigid biocompatible material such as stainless steel or polyimide, for example. The housing 120 may be cylindrical or may have a circular or any other cross sectional shape. One or both of the proximal end 124 and distal end 122 may be flat (having a planar surface perpendicular to the longitudinal axis of the housing 120) and may be squared or blunted or alternatively may tapered. The proximal end 124 includes a proximal aperture 126 to allow passage of the communication channel 60 from the sensor 110 to outside of the housing 120. The housing 120 also includes a distal aperture 128 to allow the sensor 110 to sense physiological data such as pressure. The distal aperture 128 may be in the distal end 122 of the housing 120, whether the end 128 is flat or tapered, or alternatively may be on another outer surface of the housing, such as on the side or top of the housing at or near the sensor and where it can provide communication with the surrounding environment.

The first cavity 130 is a space which surrounds at least the sensing portion of the sensor, such as the diaphragm of the pressure sensor 110 at the distal end 112 of the pressure sensor 110. The distal aperture 128 of the housing 120 adjoins the first cavity 130 so that the sensor 110 can detect physiological data through the distal aperture 128 and the first cavity 130. In the embodiment shown, the first cavity 130 is formed by the space in that portion of the housing 120 between the distal end 112 of the sensor 110 and the distal end 122 of the housing 120 where the distal aperture 128 is located.

In order to facilitate movement and placement of the device 10 in the anatomical (e.g., vascular) structure of the patient, the housing 120 is surrounded around its outer walls (except the wall adjoining the distal sleeve 20) by a filler 140 which includes a tapered distal end 142. The proximal end 144 may also be tapered. For example, as shown in FIGS. 2 and 3, the distal end 122 of the housing 120 is perpendicular to the longitudinal axis of the housing 120 and the distal sleeve 20 and therefore would be a blunt surface which would create resistance when moved into position in a vascular structure. However, it can further be seen that filler 140 forms a tapered distal end 142 such that the sensor assembly 100 forms a smoother, tapered structure that is easier to navigate through anatomical (e.g., vascular) structures and passages in a patient (e.g., it allows the device 10 to slide through vascular passages such as arterial walls without catching or snagging). In the embodiment shown, housing 120 is tapered at its proximal end 124 around the proximal aperture 126, and the filler 140 provides additional tapering to form a smooth tapered surface down to the distal sleeve 20 proximal to the housing 120.

In the embodiment shown, the proximal end 124 of the filler 140 extends around the distal sleeve 20 and extends distal to the distal end 22 of the distal sleeve 20. In alternative embodiments, the entire length of the filler 140 may extend around less or more of the distal sleeve 20 (or other structure on which the sensor assembly is located), such as encircling the distal sleeve 20 or other structure along the length of the filler 140 or not encircling the distal sleeve 20 or other support structure at any portion of the filler 140. In addition, the distal end 142 of the filler 140 may alternatively be proximal to the distal end 22 of the distal sleeve 20.

The filler 140 includes a cavity which is the second cavity 150. The second cavity 150 extends from the distal aperture 128 of the housing 120 to an opening 158 in the outer surface of the filler 140. In the embodiment shown, the longitudinal length of the second cavity 150 is less than the longitudinal length of the aperture 158. The opening 158 is located directly distal to, adjacent to, and slightly spaced apart from the distal end 122 of the housing 120 in the embodiment shown. In addition, the distal end 152 of the second cavity 150 extends distal of the distal end 159 of the aperture 158.

The filler 140 may be comprised of a single material or more than one material. For example, in some embodiments the filler 140 includes one or more layers of material. In some embodiments, the filler 140 may include a flowable thermoplastic material such as Pebex® or other suitable material. The filler 140 acts as a tapered casing or cover on the housing 120 that forms a smooth ramp-like transition between the outermost aspect of the housing 120 and the outer surface of the distal sleeve 20.

Figure 4:
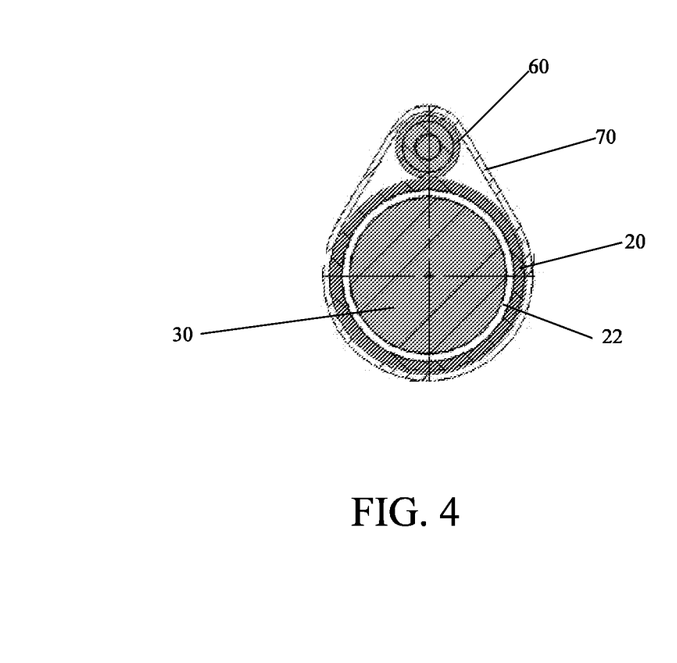
FIG. 4 is an axial cross sectional view of the sensor delivery device of FIG. 1 proximal to the sensor assembly.
Figure 5:
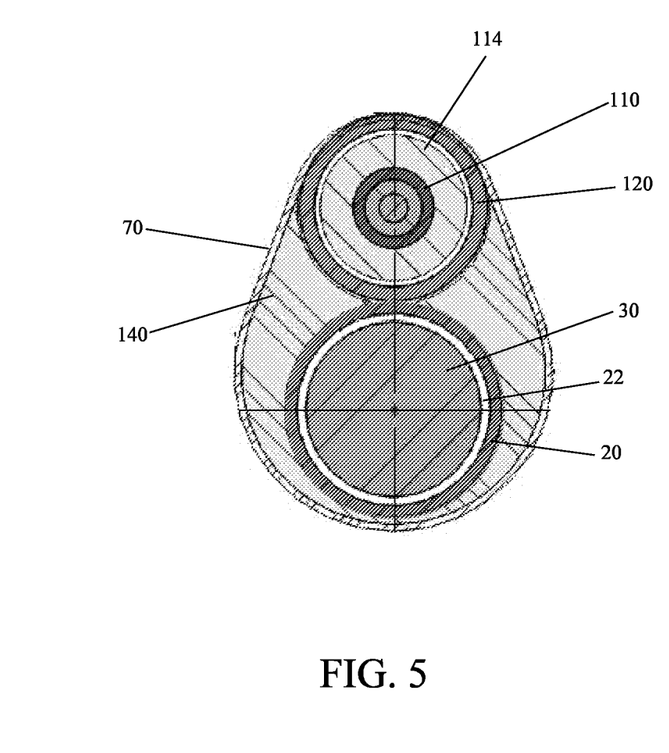
FIG. 5 is an axial cross sectional view of the sensor delivery device of FIG. 1 throughout the sensor assembly.

As shown in FIGS. 4 and 5, the sensor delivery device 10 may also include an outer layer 70, which may surround the distal sleeve 20 and the sensor assembly 100 in the form of a cover. The outer layer 70 may be a thermoplastic material which may be a heat shrunk around the filler, such as Polyethylene terephthalate (PET). The outer layer 70 may cover only the filler 140, may cover the entire sensor assembly 100 and filler, or may cover the whole distal portion of the sensor delivery device 10 including the distal sleeve 20, the communication channel 60 and the sensor assembly 100 by wrapping around outside of these components. In some embodiments, the second cavity 150 may be formed in the filler 140 and the outer layer 70 may extend across the opening 158 of the second cavity 150. The outer layer 70 may include an aperture 78 that may overlie the opening 158 of the second cavity 150 and may be the same size as and aligned with the opening 158, or may be smaller or larger than the opening 158 of the second cavity 150. In some such embodiments, the second cavity 150 is a space that is bounded by the distal end 122 of the housing 120 including the housing distal aperture 128 at the proximal end 154 of the second cavity 150. The outer surface of the distal sleeve 20 (or other support surface on which the sensor assembly 100 may be located) may form the inner surface/bottom wall of the second cavity 150. The filler 140 may form the side walls and distal wall of the second cavity 150. The outer layer 70 may form the outer surface/top wall of the second cavity 150, which may or may not also be partly formed by the filler 140. During manufacture, the outer layer 70 may be applied to the sensor delivery device 10 and the aperture 78 may be made in the outer layer after application, such as by cutting, etching, melting, or burning in the aperture at the desired location in communication with the second cavity 150. Alternatively, the aperture 78 may be present in the outer layer 70 before the outer layer 70 is applied to the sensor delivery device 10, and the aperture 78 may be aligned with the second cavity 150 as desired during manufacture when the outer layer 70 is applied to the sensor delivery device 10.

Cross sectional views of the sensor delivery device are shown in FIGS. 4 and 5. In FIG. 4, the cross section is through the distal sleeve 20, proximal to the housing 120. In FIG. 5, the cross section transects the housing 120 and the sensor 110. In FIG. 4, the communication channel 60 is shown extending along the outer surface of the distal sheath 20, and a guidewire 30 is shown within the distal sleeve 20. Both the distal sleeve 20 and the communications channel 60 are surrounded by the outer layer 70. In FIG. 5, the sensor 110 is shown within the housing 120. The housing 120 is abutting the distal sleeve 20, which encloses a guidewire 30 as in FIG. 4. The space within the housing 120 and surrounding the sensor 110 is filled with gel 114. The outer layer 30 surrounds the distal sheath 20 and the housing 120, with the filler 140 within the outer layer 70 partially surrounding both the housing 120 and the distal sleeve housing 20.

Referring back to FIG. 3, the opening 158 is located on the distal tapered end of the filler 140, while the distal aperture 128 is located on the distal end 122 of the housing 120. As a result, while the plane in which the distal aperture 128 lies is perpendicular to the longitudinal axis of housing 120 and distal sleeve 20, the plane in which the opening 158 lies is neither parallel to nor perpendicular to the plane in which the distal aperture lies. Rather, the plane in which the opening 158 is located is skewed relative to the plane of the distal aperture, with the angle being determined by the angle of the tapering of the outer surface of the filler 140 at the location of the opening 158. In the embodiment shown, the tapering of the filler 140 is very gradual, particularly at the location of the opening 158, such that the outer surface of the filler 140 at the location of the opening 158 is almost but not quite parallel to the longitudinal axis of the distal sleeve 20 and the housing 120, and is therefore almost but not quite perpendicular to the plane in which the distal aperture 128 of the housing 120 is located. In the embodiment shown, the plane in which the opening 158 is located is between about 5 and 10 degrees less than perpendicular (that is, it is about 80 to about 85 degrees) relative to the plane in which the distal aperture 128 is located.

By locating the opening in a portion of the filler 140 which is parallel to or nearly parallel to the longitudinal axis of the distal sleeve 20, it may be less likely to become snagged or to interact with or damage tissue as it is maneuvered to a location of interest. As such, the plane of the outer surface of the filler 140 at the location of the opening 158 may angle inwardly as it extends distally toward the longitudinal axis of the distal sleeve 20 and the housing 120 at an angle of between about 45 to 0 degrees, such as between about 30 to 1 degree, or about 25 to 5 degrees, or about 5 to 20 degrees relative to the longitudinal axis of distal sleeve 20 and the housing 120. The filler 140 may taper inwardly at a constant angle or the angle may vary as it extends distally and may include one or more positions in which it is parallel to the longitudinal axis of the distal sleeve or other support structure. The result is that the cross-sectional area (perpendicular to the longitudinal axis of the distal sleeve 70) of the device 10 decreases at a constant or varying rate from where it abuts the distal end of the housing 122 to the distal end of the filler 142, optionally with one or more plateaus in which the cross-sectional area is stable.

The size of the opening 158 of the second cavity 150 (which may be expressed in terms of diameter or cross sectional area) as well as the volume of the second cavity 150 may be important to obtaining accurate pressure measurements. In particular, the pulsatile nature of blood flow, cycling between a diastolic and systolic pressure can complicate the pressure measurements, making the size of the opening 158 more important. For example, if the size of the opening 158 is too small, there may be dampening or clipping of the pressure measurements which may be caused by air bubbles, for example, which may be due to air moving from the interior of the second cavity 158 out through the opening 158. The proper size of the second cavity 150 and opening 158 must therefore balance the need to avoid trapping air and the need present the most tapered profile possible to avoid the cavity being caught in stent struts or other hard materials like calcified lesions.

In some embodiments, the length of the opening 158 (from proximal to distal end 159) in the second cavity 150 is less than the length of the second cavity 150 from the proximal 154 to distal end. In some embodiments, the opening 158 of the second cavity is distally spaced away from the distal end 152 of the housing. In some embodiments, the size of the opening 158 of the second cavity 150 may be between about 0.01 mm$^2$ and about 1.0 mm$^2$, such as between about 0.05 mm$^2$ and about 0.5 mm$^2$ or between about 0.3 mm$^2$ and about 1.0 mm$^2$, such as between about 0.4 mm$^2$ and about 0.6 mm$^2$. In some embodiments, the volume of the second cavity 150 may be between about 0.01 mm$^3$ and about 0.25 mm$^3$, such as between about 0.04 mm$^3$ and about 0.12 mm$^3$ or between about 0.015 mm$^3$ and about 0.07 mm$^3$, such as between about 0.02 mm$^3$ and about 0.03 mm$^3$. In some embodiments, the ratio of the cross sectional area of the aperture of the second cavity to the volume of the second cavity is between about 0.1 and about 10, such as between about 0.5 and about 2, or between about 3 and about 5, such as between about 4.2 and about 4.4.

In some embodiments, the inside portion of the housing 120, including the first cavity 130 may be filled with a gel 114, such as a silicone dielectric gel. The second cavity 150 may also be filled with a gel. Silicone dielectric gels are often used with solid state sensors to protect the sensor from the effects of exposure to a fluid medium, for example. If the first cavity 130 is filled with a gel in front of the sensor diaphragm, and/or if the second cavity 150 is filled with a gel, then foreign material may be less likely to penetrate inside the housing 120. The gel may also offer added structural stability to the sensor 110, and/or may enhance the pressure-sensing characteristics of the sensor 110. Alternatively, one or both cavities 130, 150 may be vacant spaces into which blood or other fluid may flow during use. Alternatively, one or both cavities 130, 150 may be partially filled with gel and partially vacant.

In use, a guidewire, with or without a catheter, may be inserted into a patient's body though an incision to access a vascular structure. The guidewire (and catheter, if present) may then be navigated through the vasculature, such as through the arteries, to a location of interest, such as a location within the coronary arteries in order to evaluate the arteries for the presence of, or the severity of, a stenotic lesion. If not already present, a catheter may then be advanced over the guidewire. In some embodiments, the guidewire itself includes a sensor assembly located on the guidewire. In other embodiments, the sensor assembly may be located on the outer surface of the catheter. In still other embodiments, the sensor assembly may be located on the outer surface of a sensor delivery device such as a distal sleeve as described herein, and the sensor delivery device may be delivered to the location of interest by sliding the sensor delivery device along the guidewire, optimally within the catheter, if present, and exiting the distal end of the catheter at a location proximal to the location of interest such that the sensor can make the physiological measurement at the location of interest. Alternatively, the sensor delivery device may be delivered to the location of interest without the use of the catheter by placing the guidewire as described, removing the catheter if present, and then sliding the sensor delivery device along the guidewire.

Once the sensor is positioned at the location of interest, a pressure measurement may be taken. The location of interest may be a stenotic lesion, and the pressure measurement may be taken downstream (distal) of the stenotic lesion. A pressure measurement may also be taken upstream (proximal) of the stenotic lesion, such by using the same sensor (such as by repositioning the sensor) or by using a separate (such as a second) sensor on the same sensor delivery device, such that a first (distal) sensor is located distal to the stenosis and the second (proximal) sensor is located proximal to the stenosis. The proximal and distal pressure measurements may be used to calculate a fractional flow reserve (FFR), and this calculation may be used by a clinician to decide whether or not an intervention (such as a placement of a stent) is required. Alternatively, the location of interest may be a heart valve, and pressure measurements may be obtained proximal and/or distal to the heart valve to assess the functioning of the heart valve. Other pressure measurements may be obtained in other locations to assess for clinical evaluation.

Figure 6:
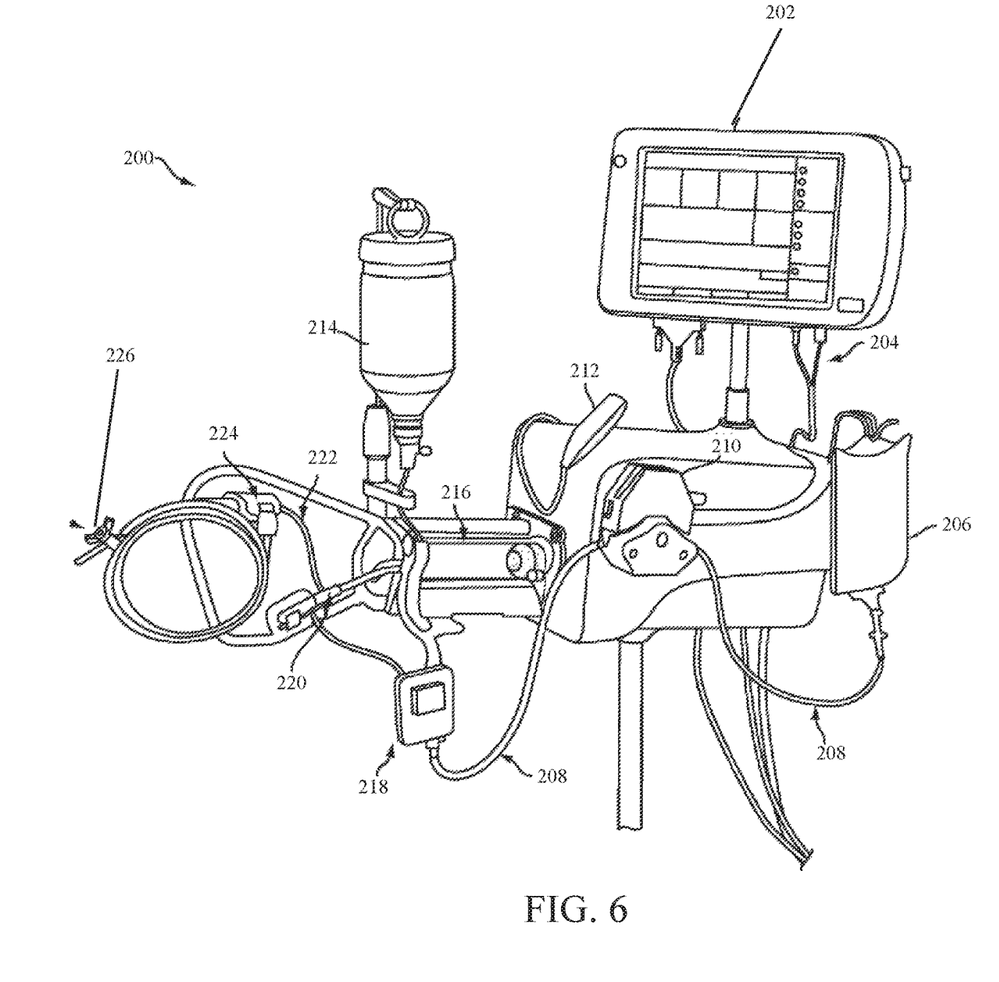
FIG. 6 is a schematic view of a contrast injection system for use with sensor delivery device and a sensor assembly according to various embodiments.

Sensor assemblies according to various embodiments may be used with powered injector systems, such as the powered injection system shown in FIG. 6. The powered injector system may be used to perform various functions and, when operable, may be coupled (e.g. by electronic signal communication) to a physiological sensor delivery device including a sensor assembly, such as the various embodiments of a sensor delivery device described above. The powered injection system 200 may be used to inject medical fluid, such as contrast media or saline, into a patient within the sterile field during a medical procedure (such as during an angiographic or CT procedure). A physiological sensor delivery device including a sensor assembly may be coupled to the system 200 and used within the sterile field during a patient procedure. The system 200 may include various components, such as a control panel 202, a hand-controller connection 204, a hand controller 212, a fluid reservoir 206, tubing 208, a pump 210, a pressure transducer 218, a fluid reservoir 214, an injection syringe 216, high pressure injection tubing 222, a valve 220, an air detector 224, and a stopcock 226. In some embodiments, the injection syringe 216 (along with its associated plunger), which is a pumping device, may be replaced with another form of pumping device that delivers high-pressure fluid injections to a patient and may be capable of operating or functioning in different, or multiple, operational modes.

The foregoing description addresses examples encompassing the principles of various embodiments. The embodiments may be changed, modified and/or implemented using various types of arrangements. In particular, one or more embodiments may be combined in a single inlet valve system. Those skilled in the art will readily recognize various modifications and changes that may be made to these embodiments without strictly following the exemplary embodiments and applications illustrated and described herein. Accordingly, it is not intended that the invention be limited, except as by the appended claims.

The invention claimed is:

1. A sensor delivery device for monitoring a fluid pressure within a vascular structure of a patient, the sensor delivery device comprising:
   an elongated tubular sheath sized for sliding along a guidewire, the sheath having a first surface;
   a sensor assembly comprising:
      a fiber optic sensor;
      a housing surrounding the sensor, the housing comprising a proximal end having a proximal aperture, a distal end, a second surface between the proximal end and the distal end, the second surface adjoined to the first surface of the sheath, and a third surface between the proximal end and the distal end, the third surface radially spaced from the second surface and defining a first aperture along a portion thereof;
      a filler outside of the housing and extending at least distally from the distal end of the housing, the filler having an outer surface that tapers inward toward the first surface of the sheath as the filler extends distally; and
   an optical fiber extending along the first surface of the sheath, passing through the proximal aperture of the housing and adjoined to the sensor at a distal end of the optical fiber.

2. The sensor delivery device of claim 1, wherein the second surface is an inner surface of the housing, and wherein the third surface is a side surface of the housing radially spaced less than 180 degrees from the second surface.

3. The sensor delivery device of claim 1, wherein the second surface is an inner surface of the housing, and wherein the third surface is an outer surface of the housing opposite the inner surface of the housing.

4. The sensor delivery device of claim 3, wherein the outer surface of the housing is a top surface of the housing.

5. The sensor delivery device of claim 1, wherein the first aperture is at a location along the third surface of the housing that is aligned with a location of the fiber optic sensor.

6. The sensor delivery device of claim 1, wherein the first aperture is at a location along the third surface of the housing that is near a location of the fiber optic sensor.

7. The sensor delivery device of claim 1, wherein the third surface defines a second aperture along a portion thereof.

8. The sensor delivery device of claim 1, wherein the sensor assembly further comprises a first cavity surrounding a sensing portion of the fiber optic sensor.

9. The sensor delivery device of claim 8, wherein the first aperture is in fluid communication with the first cavity.

10. The sensor delivery device of claim 8, wherein the first cavity is defined at least in part between a distal end of the fiber optic sensor and the distal end of the housing.

11. The sensor delivery device of claim 1, wherein the filler further extends proximally from the proximal end of the housing, the outer surface of the filler tapering inward toward the first surface of the sheath as the filler extends proximally.

12. The sensor delivery device of claim 1, further comprising an outer layer overlying the housing and the filler, the outer layer comprising a third aperture overlying the first aperture.

13. The sensor delivery device of claim 12, wherein the outer layer encircles the sensor assembly, the sheath, and the optical fiber.

14. The sensor delivery device of claim 1, wherein the fiber optic sensor comprises a pressure sensor.

15. The sensor delivery device of claim 1, wherein the sheath comprises a distal sleeve, the sensor delivery device further comprising a proximal portion adjoined to the distal sleeve, wherein the optical fiber extends within the proximal portion, and wherein the proximal portion is configured to be separate from the guidewire.

16. A method of measuring intravascular pressure in a patient at a location of interest, the method comprising the steps of:

inserting a sensor delivery device into the patient's vasculature, the sensor delivery device comprising:
   an elongated tubular sheath sized for sliding along a guidewire, the sheath having a first surface; and
   a sensor assembly comprising:
      a fiber optic sensor;
      a housing surrounding the sensor, the housing comprising a proximal end having a proximal aperture, a distal end, a second surface between the proximal end and the distal end, the second surface adjoined to the first surface of the sheath, and a third surface between the proximal end and the distal end, the third surface radially spaced from the second surface and defining a first aperture along a portion thereof;
      a filler outside of the housing and extending at least distally from the distal end of the housing, the filler having an outer surface that tapers inward toward the first surface of the sheath as the filler extends distally; and
      an optical fiber extending along the first surface of the sheath, passing through the proximal aperture of the housing and adjoined to the sensor at a distal end of the optical fiber;
advancing the sensor delivery device to the location of interest; and
measuring the intravascular pressure at the location of interest using the fiber optic sensor.

17. The method of claim 16, wherein measuring the intravascular pressure using the fiber optic sensor comprises communicating fluid from the location of interest through the first aperture into a first cavity surrounding a sensing portion of the fiber optic sensor.

18. The method of claim 16, wherein the sensor delivery device further comprises an outer layer overlying the housing and the filler, the outer layer comprising a second aperture overlying the first aperture, and wherein measuring the intravascular pressure using the fiber optic sensor comprises communicating fluid from the location of interest through the second aperture, through the first aperture, and into a first cavity surrounding a sensing portion of the fiber optic sensor.

19. The method of claim 16, wherein the second surface is an inner surface of the housing, and wherein the third surface is a side surface of the housing radially spaced less than 180 degrees from the second surface.

20. The method of claim 16, wherein the second surface is an inner surface of the housing, and wherein the third surface is an outer surface of the housing opposite the inner surface of the housing.

* * * * *